US012746487B2

(12) United States Patent
Lanier et al.

(10) Patent No.: US 12,746,487 B2
(45) Date of Patent: Sep. 29, 2026

(54) HARD CRACKING POINT OF CANNABINOIDS

(71) Applicant: CHEMTOR, LP, Lockhart, TX (US)

(72) Inventors: William Lanier, West Jordan, UT (US); Michael Peter Noll, III, Denver, CO (US)

(73) Assignee: Chemtor, LP, Lockhart, TX (US)

( * ) Notice: Subject to any disclaimer, the term of this patent is extended or adjusted under 35 U.S.C. 154(b) by 0 days.

(21) Appl. No.: 18/167,505

(22) Filed: Feb. 10, 2023

(65) Prior Publication Data

US 2023/0182037 A1 Jun. 15, 2023

Related U.S. Application Data

(63) Continuation of application No. PCT/US2022/070812, filed on Feb. 24, 2022.

(60) Provisional application No. 63/153,098, filed on Feb. 24, 2021.

(51) Int. Cl.

| | |
|---|---|
| ***A61K 31/00*** | (2006.01) |
| ***B01D 1/14*** | (2006.01) |
| ***B01D 9/00*** | (2006.01) |
| ***B01D 15/08*** | (2006.01) |

(52) U.S. Cl.

CPC .............. *A61K 31/658* (2023.05); *B01D 1/14* (2013.01); *B01D 9/0018* (2013.01); *B01D 15/08* (2013.01)

(58) Field of Classification Search

None

See application file for complete search history.

(56) References Cited

U.S. PATENT DOCUMENTS

| | | | |
|---|---|---|---|
| 9,765,000 B2 | 9/2017 | Nadal Roura | |
| 10,207,198 B2 | 2/2019 | Nadal Roura | |
| 11,198,107 B2 | 12/2021 | Davis et al. | |
| 2005/0266108 A1 | 12/2005 | Flockhart et al. | |
| 2006/0231490 A1* | 10/2006 | Manna | B01D 11/0449 210/182 |
| 2010/0168448 A1 | 7/2010 | Flockhart et al. | |
| 2019/0077782 A1 | 3/2019 | Raber et al. | |

FOREIGN PATENT DOCUMENTS

| | | |
|---|---|---|
| WO | WO 2016/153347 A1 | 9/2016 |
| WO | WO 2020/234675 A1 | 11/2020 |

OTHER PUBLICATIONS

International Search Report and Written Opinion of the International Search Authority issued by the U.S. Patent and Trademark Office for International Application No. PCT/US2022/070812 dated May 13, 2022. (8 pages).

* cited by examiner

*Primary Examiner* — Kara M Peo
(74) *Attorney, Agent, or Firm* — Haynes and Boone, LLP

(57) ABSTRACT

A method for utilizing the hard cracking of cannabinoids includes providing a substantially pure cannabinoid isolate; optionally, adding terpenes or other flavor additives; optionally, physically mixing the combination; heating the isolate or mixture to a hard cracking point of the cannabinoid for a period of time; rapidly cooling to form a crystalline cannabinoid.

16 Claims, No Drawings

HARD CRACKING POINT OF CANNABINOIDS

CROSS-REFERENCE TO RELATED APPLICATIONS

The present application is a continuation of PCT International Application No. PCT/US2022/070812 filed Feb. 24, 2022, and entitled "HARD CRACKING POINT OF CANNABINOIDS", which claims priority to U.S. Provisional Application No. 63/153,098 filed Feb. 24, 2021, and entitled "HARD CRACKING POINT OF CANNABINOIDS," the entirety of which are hereby incorporated by reference.

TECHNICAL FIELD

The present disclosure is related to using the hard cracking point of highly refined cannabinoids. More particularly, this disclosure is related to methods and systems for producing large, high purity hard candy style compositions of cannabinoid acids.

BACKGROUND

Cannabinoids occur in the hemp plant, *Cannabis sativa*, primarily in the form of cannabinoid carboxylic acids (referred to herein as "cannabinoid acids"). The more abundant forms of acid cannabinoids include tetrahydrocannabinolic acid (THCA), cannabidiolic acid (CBDA), cannabigerolic acid (CBGA) and cannabichromic acid (CBCA). Other acid cannabinoids include, but are not limited to, tetrahydrocannabivaric acid (THCVA), cannabidivaric acid (CBDVA), cannabigerovaric acid (CBGVA) and cannabichromevaric acid (CBCVA), "Neutral cannabinoids" are derived by decarboxylation of their corresponding cannabinoid acids. The more abundant forms of neutral cannabinoids include tetrahydrocannabinol (THC), cannabidiol (CBD), cannabigerol (CBG) and cannabichromene (CBC). Other neutral cannabinoids include, but are not limited to, tetrahydrocannabivarin (THCV), cannabidivarin (CBDV), cannabigerovarin (CBGV), cannabichromevarin (CBCV) and cannabivarin (CBV).

There are several examples of methods to prepare crystalline extracts of various cannabinoids from the crude oil extracts of the *Cannabis sativa* plant. For instance, U.S. Patent Application Publication No. 2005/0266108 A1, the disclosure of which is incorporated herein in its entirety, describes methods for the production of enriched extracts of THCA, CBDA, THCV, CBG and CBC as crystalline solids. U.S. Pat. No. 9,765,000 B2, the disclosure of which is incorporated herein in its entirety, describes the uses of multiple rounds of recrystallization of crude extracts as a method to prepare substantially pure isolates of THC, THCA, THCV, CBD, CBDA, CBDV, CBG and CBGA.

Currently, processing of *Cannabis* for products such as CBD isolate typically includes a preliminary step of decarboxylating the cannabinoid acids to form neutral cannabinoids. The heat associated with short path, wiped film, and other distillation methods used to purify cannabinoids decarboxylates the acid cannabinoids to produce neutral cannabinoid isolates. The use of these methods is due to the desirability of the neutral cannabinoids in the bulk market and the difficulty of separating the cannabinoid acids from the neutral cannabinoids. As such, high purity crystal isolates of cannabinoid acids are less available on the market and, if available, are very expensive. The products which are available are small crystals and generally 95% or less in purity. Accordingly, there remains a need for an economical method of preparing high-purity solid aggregates of cannabinoid acids.

DETAILED DESCRIPTION

The following descriptions are provided to explain and illustrate embodiments of the present disclosure. The described examples and embodiments should not be construed to limit the present disclosure. The basis of the disclosure is a technique developed to produce large solid cannabinoid acid formations by taking them to their hard cracking point.

According to one or more embodiments, *cannabis* oil extracted using either a polar or a non-polar hydrocarbon solvent, such as propane, butane, pentane, hexane, heptane, ethanol, methanol, ethyl acetate, critical CO2 etc. is the starting material for the disclosed method. In one or more embodiments, the starting oil should have a single acid cannabinoid present at a concentration of at least 50 wt %, at least 55 wt %, at least 60 wt %, at least 62 wt %, at least 64 wt %, at least 65 wt %, at least 67 wt %, at least 70 wt %, at least 75 wt %, or at least 80 wt %. While lower quality oils can be used, they may require a pretreatment, such as processing through a fiber film conduit reactor (such as that disclosed in U.S. Pat. No. 11,198,107, the entirety of which is herein incorporated by reference), to enrich the acid cannabinoids to the desired level. Currently, commercial breeding has produced specific *Cannabis* strains that produce high levels of THCA, CBDA, CBGA, CBCA, THCVA, CBDVA or CBGVA.

In one or more embodiments, the high concentration (i.e., at least 65 wt %) starting material is subjected to flash chromatography to separate the desired acid cannabinoid from all other cannabinoids and any plant-derived impurities present in the oil. One of ordinary skill in the art will recognize that the exact mixture of solvents used for the flash chromatography will vary depending on the cannabinoid of interest, the purity of the starting material, and the material used to pack the flash column. In fact, the desired separation can be achieved using a variety of chromatographic techniques in addition to flash chromatography, such as High-performance liquid chromatography (HPLC), Centrifugal Partition Chromatography (CPC), Countercurrent Chromatography (CCC), and by placing chromatography in line with hydrocarbon extraction equipment. Some of these chromatographic separation techniques have the ability to produce high purity extracts of individual cannabinoids even when the starting material is a complex mixture of multiple cannabinoid species.

In one or more embodiments, the chromatography step uses butane, or a mixture of butane and propane extracted oil rich in cannabinoid acids, the solvents used are pentane and methanol, and the column packing material is uncapped silica. In another embodiment, reverse phase or ion exchange chromatography may be used under solvent systems including, but not limited to ethyl acetate, ethanol, methanol, heptane and water. The peak representing the purified cannabinoid of interest is isolated from the output of the chromatography unit, and all residual solvent carried over from the chromatography process is removed using a rotary evaporator or membrane filter partitioning or is crashed out of solution using an antisolvent. In other embodiments, hydrocarbon extraction equipment is fitted with a chromatography module that precedes a collection vessel. According to this configuration, the collection vessel is placed under negative vacuum to remove the residual hydrocarbons and lend to a high quality crystalline starting material.

In one or more embodiments, the purified cannabinoid may be resuspended in an appropriate solvent such as a hydrocarbon, alcohol, ether, ester, chloroform or dichloromethane one or more times during the evaporation process in order to wash the cannabinoid material to remove any other residual solvents. Properly executing these steps will produce a high purity (i.e., at least 97 wt %, at least 98 wt %, at least 99 wt %, or greater than 99 wt % of a single acid cannabinoid) crystalline powder ("isolate"). Unlike previously disclosed methods, this isolate is the starting point for the production of large, high-purity cannabinoid solids using a hard cracking point thereof.

The use of a isolate has important implications for the production of large crystal lattices and solid aggregates utilizing the hard cracking point of the specific cannabinoid, much like the process of making hard candies with sugar. The presently disclosed approach removes the need to perform recrystallization techniques required to grow cannabinoid crystal structures. This process can be performed with any cannabinoid that is refined into a powder through a variety of techniques, such as those exemplified above. Although the present disclosure focuses on acidic, non-decarboxylated cannabinoids, the process disclosed herein may be applied to other cannabinoids as well as the neutral forms of the aforementioned cannabinoids that form a crystalline powder.

Utilizing the hard cracking point includes heating the isolate to a melting point thereof for a period of time and then rapidly cooling the material. In some embodiments, the isolate may include an additive including, but not limited to, non-cannabinoid terpenes, terpenes isolated from *cannabis* or hemp, food additives for flavor (flavoring agent), coloring agents, and/or essential oils. For example, terpene profiles, being *cannabis*-derived or of some other botanical or synthetic origin, can be added back to the starting crystalline cannabinoids to generate profiles of specific indica or *sativa* strains of *cannabis*. Additionally, food grade flavor additives such as those used to create pumpkin and spice flavor profiles and/or peppermint oils may be utilized to create seasonal variations of crystalline composites. In such embodiments, the melting point may be that of the mixture. In some embodiments, the additive is mixed in an amount, based on a total weight of the isolate and the one or more additives, of at most 20 wt %, at most 15 wt %, at most 10 wt %, at most 5 wt %, at most 3 wt %, or at most 1 wt %. The concentration of the additive may be tailored to the desired effect in the case of *cannabis*-derived terpenes or to the desired strength of the flavor when food based flavor additives or essential oils are used.

The heating step may be conducted until total melting of the material is observed; this may yield a higher clarity crystalline product. In some embodiments, the heating step is conducted at a temperature equal to or above the melting point of the material and below the boiling point of the material. In some embodiments, the heating step is conducted for 15 minutes to 2 hours, 20 minutes to 90 minutes, 30 minutes to 1 hour, at least 15 minutes, at least 20 minutes, at least 25 minutes, at least 30 minutes, or about 30 minutes. The heating step can utilize any heat source, such as an oven. In some embodiments, the heating step may be conducted under controlled pressure, which may be at, above, or below, standard pressure (1 bar) and is established using the volatile nature of the additives being used as the baseline. For example, low boiling point terpenes would be better maintained in the final composite if heated under higher pressures so as to limit their loss at temperatures that exceed their boiling point. Alternatively, and when highly volatile additives are being used to augment the final composition, it is possible to add in the terpenes or a highly volatile flavor additive immediately after heating the crystalline solid and mix the additives with the melted cannabinoid just prior to being rapidly chilled.

In some embodiments, rapid cooling includes placing the heated material into a freezer at a temperature of at most −10° C., at most −15° C., at most −18° C., at most −20° C., at most −25° C., or at most −30° C., or at most −35° C., or at most −40° C., or at most −45° C., or at most −50° C., or at most −55° C., or at most −60° C., or at most −65° C., or at most −70° C., or at most −75° C., or at most −80° C. In some embodiments, the heated material may be rapidly frozen using liquid nitrogen. The rapid cooling step is conducted until the material recrystallizes. This step may be conducted for, e.g., 15 minutes to 2 hours, 20 minutes to 90 minutes, 30 minutes to 1 hour, at least 15 minutes, at least 20 minutes, at least 25 minutes, at least 30 minutes, about 30 minutes, or about 1 hour, taking longer at warmer temperatures and larger volumes.

Example (1) A desired amount of THCA Crystalline and/or THCA Crystalline with Terpenes and/or Flavoring is measured and weighed.

(2) The THCA Crystalline and/or THCA Crystalline with Terpenes and/or Flavoring is placed in silicone mold.

(3) The silicone mold is placed in the oven at 170° F. for 30 minutes (4) After 30 minutes, the silicone mold is removed from the oven and placed in the freezer for one hour. When absolute clarity is desired, it is possible to continue to carry the heating process through until the powder transitions completely to a liquid.

(5) After one hour in the freezer, the crystallized THCA block is pressed from the silicone mold into a clean, dry intermediary container.

Although the present disclosure has been described using preferred embodiments and optional features, modification and variation of the embodiments herein disclosed can be foreseen by those skilled in the art, and such modifications and variations are considered to be within the scope of the present disclosure. It is also to be understood that the above description is intended to be illustrative and not restrictive. Many alternative embodiments will be apparent to those of in the art upon reviewing the above description. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the disclosure. Lastly, our description herein describes the method by which we obtain the highly purified starting material. It is conceivable that other methods can be implemented to obtain the starting material used in the example.

What is claimed is:

1. A method, comprising:

pretreating a *cannabis* oil comprising a cannabinoid in a fiber film conduit reactor to provide a pretreated *cannabis* oil;

forming a powdered or crystalline cannabinoid isolate from the pretreated *cannabis* oil;

heating the powdered or crystalline cannabinoid isolate to a temperate at or above a melting point of the powdered or crystalline cannabinoid isolate to form a melted isolate; and cooling the melted isolate at a temperature of at most −10° C.

2. The method according to claim 1, further comprising physically mixing a terpene with the powdered or crystalline cannabinoid isolate prior to the heating step.

3. The method according to claim 1, further comprising physically mixing an additive with the powdered or crystalline cannabinoid isolate prior to the heating step, wherein the additive is selected from terpenes, flavoring agents, coloring agents, and/or essential oils.

4. The method according to claim 1, wherein the heating is continued until the powdered or crystalline cannabinoid isolate is completely liquified.

5. The method according to claim 4, wherein the heating step is conducted for at least 30 minutes.

6. The method according to claim 1, wherein the cannabinoid is selected from tetrahydrocannabinolic acid (THCA), cannabidiolic acid (CBDA), cannabigerolic acid (CBGA) and cannabichromic acid (CBCA), tetrahydrocannabivaric acid (THCVA), cannabidivaric acid (CBDVA), cannabigerovaric acid (CBGVA), cannabichromevaric acid (CBCVA), cannabidiol (CBD), cannabigerol (CBG) and cannabichromene (CBC), tetrahydrocannabivarin (THCV), cannabidivarin (CBDV), cannabigerovarin (CBGV), cannabichromevarin (CBCV), cannabivarin (CBV), or combinations thereof.

7. The method according to claim 1, wherein the cooling step is conducted for at least 60 minutes.

8. The method according to claim 1, further comprising physically mixing an additive with the melted isolate after the heating step and prior to the cooling step, wherein the additive is selected from terpenes, flavoring agents, coloring agents, and/or essential oils.

9. The method according to claim 1, wherein the *cannabis* oil comprises a solvent selected from propane, butane, pentane, hexane, and/or heptane.

10. The method according to claim 9, further comprising subjecting the pretreated *cannabis* oil to a chromatography process before heating to remove impurities from the pretreated *cannabis* oil.

11. The method according to claim 10, wherein the chromatography process is flash chromatography.

12. The method according to claim 10, wherein the chromatography process utilizes pentane and methanol.

13. The method according to claim 10, further comprising evaporating the solvent under a vacuum after the chromatography process.

14. The method of claim 10, wherein the powdered or crystalline cannabinoid isolate has a purity of at least 98 wt % of a single cannabinoid.

15. The method according to claim 1, wherein heating the powdered or crystalline cannabinoid isolate comprises heating the powdered or crystalline cannabinoid isolate in an oven for 15 minutes to 2 hours.

16. The method according to claim 15, wherein heating the powdered or crystalline cannabinoid isolate is conducted at a pressure above 1 bar.

* * * * *